United States Patent [19]

Rimmer

[11] 4,451,451
[45] May 29, 1984

[54] RADIOPHARMACEUTICAL COMPOSITION BASED ON TECHNETIUM-99M AND REAGENT FOR MAKING IT

[75] Inventor: John Rimmer, Amersham, England
[73] Assignee: Amersham International plc, England
[21] Appl. No.: 436,689
[22] Filed: Oct. 26, 1982

[30] Foreign Application Priority Data

Oct. 30, 1981 [GB] United Kingdom ............... 8132778

[51] Int. Cl.$^3$ .................... A61K 43/00; A61K 49/00
[52] U.S. Cl. .................................... 424/1.1; 424/9
[58] Field of Search .................................. 424/1.1, 9

[56] References Cited

U.S. PATENT DOCUMENTS

| | | | |
|---|---|---|---|
| 4,042,676 | 8/1977 | Molinski et al. | 424/1.1 |
| 4,048,296 | 9/1977 | Wolfangel et al. | 424/1.1 |
| 4,229,427 | 10/1980 | Whitehouse | 424/1.1 |
| 4,232,000 | 11/1980 | Fawzi | 424/1.1 |
| 4,233,284 | 11/1980 | Fawzi | 424/1.1 |
| 4,247,534 | 1/1981 | Bevan | 424/1.1 |
| 4,364,920 | 12/1982 | Winchell et al. | 424/1.1 |

Primary Examiner—Christine M. Nucker
Attorney, Agent, or Firm—Wenderoth, Lind & Ponack

[57] ABSTRACT

Radiopharmaceutical compositions containing complexes of technetium-99m with a complexing agent are prone to time and activity-related decomposition and formation of pertechnetate. Stabilizing agents for such complexes are organic compounds having an amine group and a carboxylic acid group attached to an aromatic ring. A preferred stabilizing agent is the sodium salt of 4-aminobenzoic acid. There are claims to a composition comprising a technetium 99-m complex stabilized by means of the said stabilizing agent; and to a reagent which forms, on addition of an aqueous solution of pertechnetate, a radiopharmaceutical composition, which reagent comprises a tin metal or stannous reducing agent for the pertechnetate, a complexing agent for the reduced technetium, for example a phosphorus-containing bone scanning agent, and a stabilizing agent as defined.

12 Claims, No Drawings

RADIOPHARMACEUTICAL COMPOSITION BASED ON TECHNETIUM-99M AND REAGENT FOR MAKING IT

The radioactive isotope technetium-99m is a gamma emitter with a half life of about 6 hours and is very widely used in medical diagnosis. Technetium-99m is generally obtained as a sterile solution of pertechnetate ion TcO4 in isotonic saline from a commercially available technetium generator. It is usually necessary to reduce the technetium from the +7 valency to the +3, +4 or +5 valency, in order to form, with a suitable complexing agent, a complex which has a desired property, e.g. upon introduction into a patient, of becoming localised in a desired organ.

The most widely used reducing agent for this purpose is stannous ion $Sn^{2+}$. Diagnostic kits frequently contain, in a sterile freeze-dried state, a mixture of stannous salt with a complexing (or chelating) agent for technetium. The kit is activated by aseptic introduction of an aliquot of generator eluate containing pertechnetate in saline. The stannous salt reduces the technetium, the complexing agent forms a complex with the reduced technetium, and the resulting sterile liquid is ready for injection into a patient. Many hospitals make up a single large batch of injection solution in the morning, which they hold for use throughout the day.

Another reducing agent for pertechnetate is tin metal as described in British Patent Specification Nos. 2,016,198 and 2,036,000. One of the features of using tin metal as a reducing agent is that there is little or no free stannous ion in solution.

These radiopharmaceutical compositions are prone to decompose on standing. The causes of this, which include oxidative and radiolytic effects, are complex and not fully understood, but two routes may be noted:

(i) These compositions are prone to regenerate pertechnetate on storage. Pertechnetate tends to be cleared only slowly from the blood and also to locate in the gut and thyroid, thus degrading the biodistribution pattern, and is thus not desired. The problem becomes acute for solutions containing high activities of Tc-99m, and the present tendency to employ larger amounts of Tc-99m in preparations aggravates the problem.

When stannous ion is used as a reducing agent, it is found that, while stannous ion remains in solution, pertechnetate is not formed. Once stannous ion has been used up (for example by oxidation by air or by radiolytic oxidation) pertechnetate begins to form. The onset of pertechnetate formation can thus be conveniently monitored by measuring the stannous ion concentration of the radiopharmaceutical composition.

When metallic tin is used as a reducing agent, it seems possible that the presence of a low concentration of stannous ion may be formed in solution and may improve the stability of the complex after its formation.

(ii) The tc-99m complex, or perhaps the complexing agent, may be prone to radiolytic decomposition.

As will be apparent, there are a number of theoretically possible ways of reducing or eliminating the problem of decomposition of the radiopharmaceutical composition:

(a) Eliminate oxygen e.g. by nitrogen purging the eluate and kit vials. This is to some extent effective but very inconvenient, particularly when using multidose vials. Technetium generator eluent is often saturated with air in order to maintain generator yields; it would be tiresome to have to displace dissolved oxygen in the eluate before use.

(b) Use more stannous salt as a reducing agent. This is undesirable, because tin is mildly toxic, and because the excess tin tends to hydrolyse with the formation of technetium-tin colloids which locate in the reticuloendothelial system (liver, spleen, etc.), thus degrading the biodistribution pattern.

(c) Use an antioxidant. This is the solution advocated in a number of patent specifications, for example, British Nos. 1489330; 1530106; 1541070 and European Nos. 0004684; 0006658; 0006659 and 0007676. However, it is undesirable to have antioxidants present for this reason; they may be toxic, or they may react with the complexing agent or with the technetium and so degrade the biodistribution pattern.

For example, ascorbic acid, a known non-toxic antioxidant and one of the most favoured compounds for protecting stannous salts, forms a complex with technetium, which, in the presence of iron, yields a technetium iron ascorbate, a known kidney scanning agent.

It is an object of this invention to provide a radiopharmaceutical composition comprising technetium-99m present in a valency state greater than 0 and less than 7, stabilized by means of an agent which is nontoxic and which does not spoil the distribution pattern of the technetium-99m.

According to the present invention, such stabilizing agents are organic compounds having an amine group and a carboxylic acid group attached to an aromatic ring. Such compounds may have the formula:

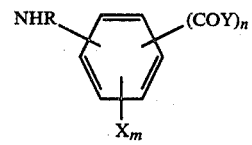

where
R is C1–C6 alkyl or hydrogen,
X is C1–C6 alkyl or OH,
m is 0, 1 or 2,
Y is OH or —NH.CH2.COOH,
n is 1 or 2
and salts, esters and amides of such compounds.

Preferably X is alkyl. Preferably, the number of reactive groups is sufficiently low to avoid risk of formation of complexes with technetium.

Examples of such compounds are
2-aminobenzoic acid
3-aminobenzoic acid
4-aminobenzoic acid
4-methylaminobenzoic acid
3,5-diaminobenzoic acid
4-aminosalicylic acid
4-aminohippuric acid Of these, 4-aminobenzoic acid (PAB) is the preferred compound. PAB is a naturally occurring substance, present in yeast, and known as Vitamin $B_x$. It has very low toxicity (L.D.50 6 g/kg in rats). It is used as a sun-screen agent.

It is believed that these stabilizing agents operate to reduce or prevent decomposition mainly or exclusively by route (i) above. They are therefore used to particular advantage in radiopharmaceutical compositions containing Tc-99m complexes that are prone to decomposition by this route. Among these may be mentioned phosphorus-containing bone scanning agents such as the complexes of Tc-99m with methylene diphosphonate, pyrophosphate, hydroxymethane diphosphonate, hydroxyethane diphosphonate, aminoethane diphosphonates, and 2,3-dicarboxypropane-1,1-diphosphonic acid; kidney visualisation agents such as technetium-99m complexes with dimercaptosuccinic acid; brain and kidney function agents such as technetium-99m complexes with diethylenetriamine pentaacetic acid and thiodiglycollic acid; and hepatobiliary agents such as technetium-99m complexes with mercapto isobutyric acid and pyridoxylideneamino acid. Other examples will immediately occur to those skilled in the art. The invention is applicable to complexing agents that form insoluble particulate complexes with technetium, but is of particular benefit for complexing agents, such as those listed above, which form soluble complexes with technetium.

This invention also envisages a reagent which forms, on addition of an aqueous solution of pertechnetate, a radiopharmaceutical composition, which reagent comprises a tin metal or stannous tin reducing agent for the pertechnetate, a complexing agent for the reduced technetium, and a stabilizing agent as defined above. When the reducing agent used is stannous ion, the stabilizing agent should preferably be such, and be present in an amount to, diminish oxidation of $Sn^{2+}$ to $Sn^{4+}$ during preparation and storage of the reagent and of the radiopharmaceutical composition.

Such reagents are generally made by preparing in bulk an aqueous solution of the reducing agent (when a stannous salt is used), and the complexing agent, dispensing aliquots of the solution into vials, freeze-drying, capping the vials under nitrogen, and sterilizing them by gamma-radiation. The stabilizing agent may conveniently be added to the bulk aqueous solution.

The sterile freeze-dried reagent is later reactivated by the user by adding technetium generator eluate, typically containing up to 500 mCi of technetium as pertechnetate. Alternatively but less preferably the stabilizing agent may be incorporated in the technetium generator eluate.

It is desirable that the stabilizing agent should be water-soluble, so that it is present in aqueous solution during formation and storage of the technetium complex. For this reason, salts of the amino-aromatic carboxylic acids are often preferable to the acids themselves or to esters or amides thereof. Suitable cations of such salts include sodium, potassium and ammonium. It may be convenient to use stannous salts, Radiopharmaceutical compositions containing up to 500 mCi of Tc-99m may be stabilized by from 0.1 to 10 mg, preferably 0.5 to 6 mg, of the stabilizing agent. The upper limits are not critical, but little extra effect is achieved with higher levels, and there is always the risk of side reactions. The concentration of some stabilizing agents, such as 2-aminobenzoic acids and 1, 2-dicarboxylic acids may need to be chosen with care to avoid the risk that the stabilizing agent may complex the reduced technetium instead of the intended complexing agent. In general, the more $Sn^{2+}$ that is present, the less stabilizing agent is needed. For compositions containing more than 500 mCi of Tc-99m, higher quantities of stabilizing agent may be required.

In the same way, reagents according to the invention which are intended for reactivation by generator eluate containing up to 500 mCi of Tc-99m, may contain from 0.1 to 10 mg, preferably 0.5 to 6 mg, of the stabilizing agent.

Naturally, the amount of reducing agent and complexing agent used will depend on the nature of these reagents. Typically, however, from 0.1 to 1.0 mg of stannous reducing agent and from 0.3–20 mg of complexing agent will be found appropriate for solutions containing up to 500 mCi of technetium-99m.

Our European Patent Application No. 81303608.4 describes the use of nitrate and nitrite as stabilizing agents for radiopharmaceutical compositions containing complexes of Tc-99m in a valency less than 7. The stabilizing agents of the present invention may conveniently be used in conjunction with nitrate or nitrite.

The following Examples illustrate the invention. In these Examples, results are expressed in terms of pertechnetate (Tc-99m) content as a percent of the total technetium-99m present. Differences below 1% are not significant. A composition which gave a pertechnetate content above 1% would not be considered acceptable in commercial operation. However, where contents are only marginally over 1%, e.g. less than 5%, minor adjustment of proportions will usually suffice to bring the figure down below 1%.

EXAMPLE 1

A bulk solution containing stannous fluoride, methylene diphosphonate (MDP) and the chosen stabilizing agent was made up. Aliquots were dispensed into vials so that each vial contained 0.34 mg of $SnF_2$, 5 mg of MDP and 2.0 mg of the stabilizing agent. The vials were freeze-dried. In some cases they were sterilized by gamma-radiation. The reagent was reconstituted by adding enough technetium generator eluate to provide 200 mCi of technetium per tube. The concentration of pertechnetate was measured immediately after reconstitution and again 6 hours later.

The results are set out in the following Table 1. Pertechnetate was measured by thin layer chromatography on hydroxyapatite.

TABLE 1

| Stabilizing agent | Vial Sterilized | Tc-99m as Pertechnetate (%) | |
|---|---|---|---|
| | | after 0 hrs. | after 6 hrs. |
| None | No | 0 | 6.7 |
| None | Yes | 0 | 11.7 |
| 4-aminobenzoic acid | Yes | 0.2 | 1.0 |
| 4-aminobenzoic acid | No | 0.0 | 0.1 |
| Sodium 4 - aminobenzoate | No | 0.0 | 0.2 |
| Sodium 4 - aminobenzoate | Yes | 0.1 | 0.0 |
| 4 - aminohippuric acid | No | 0.0 | 0.0 |
| 4 - methylaminobenzoic acid | No | 0.0 | 0.0 |
| 3, 5 - diaminobenzoic acid | No | 0.0 | 0.3 |
| 3 - aminobenzoic acid | No | 0.1 | 0.1 |
| 2 - aminobenzoic acid | No | 0.2 | 0.8 |
| 4 - aminosalicylic acid | No | 0.0 | 0.0 |

EXAMPLE 2

Solutions containing stannous fluoride, MDP and sodium 4-aminobenzoate were dispensed into vials to provide 0.34 mg $SnF_2$ (257 micrograms of $Sn^{2+}$) and 5 mg MDP per vial. The vials were freeze-dried, and the $Sn^{2+}$ content of some of the vials determined by starch-iodine titration. The results are set out in Table 2.

TABLE 2

| Amount of Stabilizing Agent (mg) | Amount of $Sn^{2+}$ (μg) | % loss of $Sn^{2+}$ |
| --- | --- | --- |
| 0 | 217 | 15 |
| 0.5 | 249 | 3 |
| 1 | 249 | 3 |
| 2 | 249 | 3 |

Other vials were reconstituted by means of technetium generator eluate to various activities in the range 200 mCi to 450 mCi. The resulting radiopharmaceutical compositions were allowed to stand for 6 hours and were then tested for pertechnetate content with the results shown in Table 3.

TABLE 3

| Amount of Stabilizing Agent (mg) | Activity of Reconstituted Composition (mCi) | Tc-99m as Pertechnetate (%) |
| --- | --- | --- |
| 0 | 200 | ~20 |
| 0.5 | 200 | 0.1 |
| 0.5 | 400 | 0.2 |
| 0.5 | 446 | 0.0 |
| 2.0 | 416 | 0.0 |

Yet other vials were reconstituted with 8 ml of generator eluate and allowed to stand for 6 hours with aeration (by bubbling 20 ml of air through the solution) at 0 and 3 hours. Pertechnetate contents are set out in Table 4.

TABLE 4

| Amount of Stabilizing Agent (mg) | Activity of Reconstituted Composition (mCi) | Tc-99m as Pertechnetate (%) |
| --- | --- | --- |
| 0.0 | 250 | 23.5 |
| 0.5 | 200 | 1.0 |
| 2.0 | 200 | 0 |
| 2.0 | 250 | 0 |

EXAMPLE 3

The contents of two vials, each containing in Freeze-dried form 10 mg of 2,3-dicarboxypropane-1,1-diphosphonic acid (DPD) and 0.2 mg of stannous fluoride were dissolved in generator eluate to give two 5 ml, 218 mCi solutions. Both solutions were flushed with air. To one solution was added 2 mg of sodium 4-aminobenzoate (PAB).

15 minutes and 6 hours after reconstitution both solutions were monitored for free pertechnetate content by instant thin layer chromatography (i.t.l.c.) on silica gel impregnated glass fibre strips eluted first with methyl ethyl ketone then saline.

15 minutes after reconstitution no free pertechetate could be detected in either solution. 6 hours after reconstitution the solution containing PAB gave 0.25% $TcO_4$, the solution without PAB 10.7% $TcO_4$.

EXAMPLE 4

Biodistribution patterns in rats of four different bone scanning agents were compared. The reagents were A. A commercially available agent containing MDP and no stablizing agent but a rather high concentration of stannous ion.
B. A commercially available agent based on DPD
C. An agent according to the present invention containing 5 mg of MDP, 0.34 mg of $SnF_2$, and 2 mg of sodium 4-aminobenzoate.
D. An agent as C, but containing 2 mg of sodium ascorbate in place of the sodium 4-aminobenzoate.

Each reagent was reconstituted with generator eluate to 8 ml and 200 mCi, and in some cases allowed to stand for 6 hours. The solution was then injected into rats, which were dissected 2 hours post injection. The results set out in Table 5 below are in respect of 9 rats injected with fresh solution and 9 with 6 hour old solution.

TABLE 5

| Bone Agent | A | B | C | D |
| --- | --- | --- | --- | --- |
| Bone/Blood Ratio | 110–180 | 145–245 | 310–400 | 70–145 |
| Blood Percentage | 0.25–0.40 | 0.22–0.30 | 0.10–0.13 | 0.31–0.62 |
| Liver + Spleen Percentage (200μl injection volume) | 4.2–5.0 | 25–34 | 0–2.0 | 0–2.0 |

The biodistribution pattern of bone agent C in this experiment was superior to those of the three known bone agents.

EXAMPLE 5

Two solutions were prepared, the first containing 4 mg of 1-hydroxyethylidene-1,1-diphosphonic acid (using a solution 60% w/v in water), 0.2 mg of stannous fluoride (added dissolved in 1.0 M HCl) and 2 mg of sodium 4-aminobenzoate (added dissolved in water) and the second as the first but without the sodium 4-aminobenzoate.

Generator eluate was added to give two 5 ml solutions each with an activity of 100 mCi.

1 hour and 6 hours after reconstitution i.t.l.c. was carried out as in Example 3. At 1 hour no free pertechnetate could be detected in the solution containing sodium 4-aminobenzoate. The solution not containing sodium 4-aminobenzoate showed 6.3% pertechnetate. At 6 hours the solution with sodium 4-aminobenzoate gave 4.5% pertechnetate, the solution without gave 63.2% pertechnetate.

EXAMPLE 6

10 mg of 1-aminoethane-1,1-diphosphonic acid was dissolved in water in an air-filled vial. 0.3 stannous chloride dissolved in 1.0 M HCl and 2 mg of sodium 4-aminobenzoate dissolved in water were added. The pH of the solution was adjusted to 5.0. Generator eluate was added to give a final solution volume of 5 mls and an activity of 100 mCi.

An identical solution was prepared with the sodium 4-aminobenzoate omitted.

1 hour after reconstitution no free pertechnetate would be detected in either solution by i.t.l.c. as in the previous example.

6 hours after reconstitution the solution containing sodium 4-aminobenzoate showed 2.9% pertechnetate, the solution with the sodium 4-aminobenzoate omitted showed 70% free pertechnetate.

EXAMPLE 7

A bulk solution containing stannous chloride and calcium trisodium diethylentriamine-pentaacetic acid ($CaNa_3DTPA$) was prepared such that each milliliter of solution contained 5 mg $CaNa_3DTPA$ and 2.25 mg stannous chloride (calculated as dihydrate). The bulk solution was divided into two parts and sodium 4-aminobenzoate (PAB) was added to one part to give a concentration of stabilizer of 1 mg per milliliter. 2.0 ml aliquots of bulk solution were dispensed into separate batches of vials and freeze-dried to provide stabilized and unstabilized reagent. The reagent was reconstituted by adding enough technetium generator elulate to provide approximately 300 mCi of technetium-99m per vial. Pertechnetate content as a percentage of the total technetium content was measured at intervals from 5 minutes to 7 hours after reconstitution. The contamination of the vial contents by the entry of air (as might be expected during normal use of such a product) was deliberately created 15 minutes after reconstitution by bubbling 20 mls of air through the radioactive solution.

Pertechnetate was measured by ascending thin layer chromatography on silica gel with serial elution of samples using butan-2-one and isotonic saline. The proportion of pertechnetate, expressed as a percentage of total technetium-99m in vials containing PAB stabilizer was in all cases and at all times less than 1%. The proportion of pertechnetate in vials not containing PAB stabilizer rose in all cases above 1% in less than 2 hours and above 40% in less than 5 hours.

EXAMPLE 8

Solutions containing stannous chloride and dimercaptosuccinic acid (DMSA) were prepared such that when subdivided into nitrogen-filled vials each vial contained 200 μg stannous ion and 0.5 mg or 1 mg DMSA. In addition, 2 mg sodium 4-aminobenzoate was added to some of the vials.

For testing between 100 and 200 mCi of technetium generator eluate was added to each vial such that the total volume of the preparation was around 5 mls. Pertechnetate content of the vials, as a percentage of the total technetium-99m content was measured at intervals from 15 minutes to 6 hours. Pertechnetate was assessed by descending paper chromatography on Whatman No. 1 paper using butan-2-one as eluent.

The presence of sodium 4-aminobenzoate was found to be effective in reducing the free pertechnetate content to approximately 3% in 6 hour old preparations.

EXAMPLE 9

Into a vial was dispensed an aliquot of an aqueous solution containing 10 mg thiodiglycollic acid, 400 μg stannous fluoride, 1 mg sodium fluoride and 2 mg sodium 4-aminobenzoate. The contents were freeze-dried, and were later reconstituted in 8 mls of technetium generator eluate to an activity of 276 mCi. After 8 hours, no free pertechnetate could be detected in the solution.

EXAMPLE 10

In a clinical trial carried out in 6 hospitals in Great Britain, West Germany and Belgium over 1000 patients received injections of stabilized Tc-99m MDP agent described in Example 4 as formulation C. Injections were made from vials reconstituted with up to 600 mCi of Tc-99m pertechnetate at time intervals up to 9.½ hours after labelling. Examination of the patients with the aid of γ-cameras produced diagnostically satisfactory scintigrams in all cases with no evidence of significant levels of uncomplexed technetium in any of the administered injections.

I claim:

1. A composition comprising technetium-99m present in a valency state greater than 0 and less than 7, stabilized by means of a stabilizing agent having the general formula:

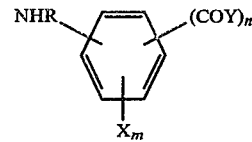

where
R is C1–C6 alkyl or hydrogen,
X is C1–C6 alkyl or OH,
m is 0, 1 or 2,
Y is OH or —NH.CH$_2$.COOH,
n is 1 or 2
or a salt, ester or amide thereof.

2. A composition as claimed in claim 1, in the form of a radiopharmaceutical composition suitable for administration to a mammal.

3. A composition as claimed in claim 1, wherein the stabilizing agent is selected from 2-aminobenzoic acid, 3-aminobenzoic acid, 4-aminobenzoic acid, 4-methylaminobenzoic acid, 3,5-diaminobenzoic acid, 4-aminosalicylic acid, and 4-aminohippuric acid and salts thereof.

4. A composition as claimed in claim 3, where in the stabilizing agent is the sodium salt of 4-aminobenzoic acid.

5. A composition as claimed in claim 1, wherein the technetium is present as a complex in a scanning agent selected from phosphorus-containing bone scanning agents, kidney visualisation agents, brain and kidney function agents, and hepatobiliary agents.

6. A composition as claimed in claim 5, wherein the technetium is present as a complex with a complexing agent selected from methylene diphosphonate, pyrophosphate, hydroxymethane diphosphonate, hydroxyethane diphosphonate, aminoethane diphosphonates, and 2,3-dicarboxypropane-1,1diphosphonic acid.

7. A composition as claimed in claim 5, wherein the technetium is present as a complex with diethylenetriamine pentaacetic acid or a salt thereof.

8. A reagent which forms, on addition of an aqueous solution of pertechnetate, a radiopharmaceutical composition according to claim 2, which reagent comprises a tin metal or stannous reducing agent for the pertechnetate, a complexing agent for the reduced technetium, and a stabilizing agent having the general formula:

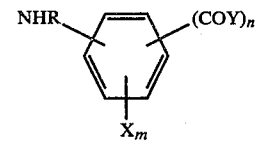

where
R is C1–C6 alkyl or hydrogen,
X is C1–C6 alkyl or OH,
m is 0, 1 or 2,
Y is OH or —NH.CH.COOH,
n is 1 or 2
or a salt, ester or amide thereof.

9. A reagent as claimed in claim 8, containing from 0.1 to 10 mg of stabilizing agent.

10. A reagent as claimed in claim 8, intended for reaction with an aqueous solution of pertechnetate having an activity of up to 500 mCi, including from 0.1 to 1.0 mg of a stannous reducing agent for the pertechnetate and from 0.5 to 6 mg of the stabilizing agent.

11. A reagent as claimed in claim 8, wherein the complexing agent is selected from methylene diphosphonate and diethylenetriamine pentaacetic acid and salts thereof.

12. A reagent as claimed in claim 8, wherein the stabilizing agent is the sodium salt of 4-aminobenzoic acid.

* * * * *